(12) United States Patent
Gueller et al.

(10) Patent No.: US 7,402,285 B2
(45) Date of Patent: Jul. 22, 2008

(54) SWITCH BLOCK HAVING AT LEAST ONE ATTACHED OR INTEGRATED REACTION VESSEL

(75) Inventors: Rolf Gueller, Herznach (CH); Josef Schröer, Muttenz (CH); Franz Metzger, Basel (CH)

(73) Assignee: Chemspeed Technologies AG, Augst (CH)

( * ) Notice: Subject to any disclaimer, the term of this patent is extended or adjusted under 35 U.S.C. 154(b) by 571 days.

(21) Appl. No.: 10/344,066

(22) PCT Filed: Jul. 26, 2001

(86) PCT No.: PCT/CH01/00461

§ 371 (c)(1),
(2), (4) Date: Feb. 6, 2003

(87) PCT Pub. No.: WO02/16034

PCT Pub. Date: Feb. 28, 2002

(65) Prior Publication Data

US 2003/0152489 A1  Aug. 14, 2003

(51) Int. Cl.
*B01L 3/00* (2006.01)
(52) U.S. Cl. .................. 422/99; 422/100; 422/101; 422/103; 436/180

(58) Field of Classification Search ........... 422/99–103; 436/180
See application file for complete search history.

(56) References Cited

U.S. PATENT DOCUMENTS 5,137,698 A    8/1992  Ansorge et al.
6,303,389 B1 * 10/2001 Levin et al. ................. 436/518

FOREIGN PATENT DOCUMENTS

| EP | 0 908236 A2 * | 2/1998 |
| EP | 0 908 236 A2 | 4/1999 |
| EP | 0 908 236 A3 | 1/2000 |
| WO | WO 98/57738 * | 12/1998 |

OTHER PUBLICATIONS

International Search Report for International Application No. PCT/CH01/00461.

* cited by examiner

*Primary Examiner*—Jill Warden
*Assistant Examiner*—Jyoti Nagpaul
(74) *Attorney, Agent, or Firm*—Welsh & Katz, Ltd.

(57) ABSTRACT

Twelve reaction vessels (2) in two parallel rows are attached to a switch block (401). The switch block (401) comprises a reaction block (403) and twelve slide plates (404), which are arranged within it and which can be adjusted between an open position, a closed position and a further position. In the open position, access in straight line to the associated reaction vessel (2) is possible whereas in the closed position, the corresponding reaction vessel (2) is closed in a pressure-tight manner by the switch block (401). In the case of a positive pressure or depression in the reaction vessel (2), the corresponding slide plate (404) is pressed by this positive pressure or depression against the reaction block (403) or is drawn onto it. By means of this switch block (401), it is also possible to carry out processes in which high positive pressures are present in the reaction vessels (2).

20 Claims, 12 Drawing Sheets

SWITCH BLOCK HAVING AT LEAST ONE ATTACHED OR INTEGRATED REACTION VESSEL

The present invention relates to a switch block having at least one attached or integrated reaction vessel, as defined in the preamble of the independent patent claim 1.

In order to carry out a plurality of chemical, biochemical, biological and physical processes in parallel, automatic laboratory units with switch blocks, to which a plurality of reaction vessels are attached, are for example used. A known switch block—such as is described, for example, in WO 98/57738 from the same applicant—comprises, at the bottom, a reaction plate, to which the reaction vessels are fastened by means of coupling parts, a slide plate as displaceable functional part resting on the reaction plate, then a mating plate and finally, in addition, a support plate. The reaction plate the mating plate and the support plate are firmly connected together, whereas the slide plate can be displaced into various positions by means of an actuation element which protrudes at an end side between the reaction plate and the mating plate. In one of these slide plate positions, the reaction vessels are sealed by the slide plate, whereas, in another, open position, access in straight line to the reaction vessels is possible. In a further position, the reaction vessels are connected to a gas duct.

These known switch blocks with reaction vessels attached to them have proved successful in practice but have the disadvantage that, in the case of a high positive pressure in the reaction vessels closed by the slide plate or connected to the gas duct, gas contained in the reaction vessels can escape. The switch blocks are therefore unsuitable for processes in which high positive pressures occur in the reaction vessels or in which the reaction vessels are subjected to high positive pressures.

In view of the fact that the previously known switch blocks with reaction vessels attached to them, as described above, cannot be employed for certain applications, the invention is based on the following object. A switch block is to be created with at least one attached or integrated reaction vessel of the type mentioned at the beginning, which switch block is also suitable for processes in which high positive pressures occur in the reaction vessel or in which the reaction vessels are subjected to high positive pressures.

This object is achieved by means of a switch block, according to the invention, having at least one attached or integrated reaction vessel, as defined in the independent patent claim 1. Preferred embodiment variants are given in the dependent patent claims.

In its essentials, the invention consists of the following: a switch block with at least one attached or integrated reaction vessel comprises a reaction block and, arranged within it, a functional part which can be at least adjusted between an open and a closed position, access in straight line being possible to the reaction vessel in the open position. According to the invention, the at least one reaction vessel is sealed in a pressure-tight manner by the switch block in the closed position of the functional part, the functional part being pressed against the reaction block or drawn onto it by the positive pressure or depression when there is a positive pressure or depression in the reaction vessel.

Because the reaction vessel or vessels is or are sealed in a pressure-tight manner in the closed position of the functional part, it is also possible to carry out processes in which high positive pressures prevail in the reaction vessel or vessels. Because, in the case of a positive pressure or depression in the reaction vessel, the functional part is pressed against or drawn onto the reaction block by this positive pressure or depression, it is also true that as the positive pressure or depression becomes higher, the functional part and the reaction block are pressed more strongly against one another, if appropriate with a sealing element between them. The positive pressure or depression itself, therefore, ensures that no gas penetrates between the functional part and the reaction block. The switch block according to the invention still seals even at very high pressures; where sufficient mechanical strength of the reaction block and functional part are present, due to their being manufactured from titanium, for example, pressures above 250 bar can be accepted.

The functional part is advantageously arranged with clearance in the reaction block so that it is not in gas-tight contact with the reaction block on at least one side, preferably the side remote from the at least one reaction vessel, at normal pressure. This permits an adjustment of the functional part at normal pressure without applying great force.

In a preferred embodiment variant, the functional part is a displaceable slide plate. Access to a plurality of parallel reaction vessels can be jointly controlled, in a simple manner, by means of a slide plate. In addition, the adjustment of the slide plate takes place by means of a linear motion which is easily realized.

In another advantageous embodiment variant, the functional part is a rotatable ball or a rotatable cylinder. Such a functional part remains at the same location during an adjustment, its space requirement is therefore small. It is then, therefore, of particular advantage where little space is available, for example when a plurality of functional parts are arranged adjacent to one another for the individual control of the access to a plurality of reaction vessels arranged adjacent to one another.

The reaction block is advantageously made up of two or more parts, which can preferably be taken apart and between which the functional part is arranged, preferably of a reaction plate and a mating plate, between which the functional part is sandwiched, and a retention profile section, which is pushed over the reaction plate and the mating plate and holds them together. The construction of the reaction block from a plurality of parts permits simple manufacture. If it can be taken apart, furthermore, it is also easier to clean.

At least one sealing element, preferably made of plastic, rubber or a rubber-like material, in particular a polyfluoridated elastomer, is preferably arranged between the reaction block and the functional part, preferably in grooves in the functional part or in the reaction block. The at least one sealing element ensures good sealing at high positive pressures. The arrangement in grooves in the functional part permits the adjustment of the functional part so that the at least one sealing element is taken along with it. The arrangement in grooves in the reaction block permits the adjustment of the functional part without the need to displace the at least one sealing element.

Simultaneously or alternatively, the mutually contacting surfaces of the functional part and the reaction block are configured, on at least one side, in such a precise manner that the surfaces are in sealing contact with one another, the surfaces being preferably treated with grease, oil or Teflon spray and the mutually contacting surfaces being preferably smaller than the complete sides facing toward one another. In this way, it is possible to dispense with separate sealing elements on the at least one side.

In order to adjust the functional part, the latter is advantageously connected to an actuation element which extends through the reaction block to the outside, the actuation element being preferably placed on the functional part in a region which is not subjected to positive pressure and depression. The adjustment of the functional part takes place most reliably by means of a mechanical actuation element. The latter is advantageously in contact with a region of the switch block which is free of positive pressure and depression so that, in the case where positive pressure or depression may be present, the latter is not degraded. Otherwise, the actuation element and/or its region in the switch block must be additionally and separately sealed by means of a seal which is difficult to realize.

In the open position of the functional part, a supply and/or removal tool and/or a probe can preferably be introduced from above through the switch block into the reaction vessel. This permits a metered addition and/or removal of substances, the supply of energy and/or the measurement of parameters while a reaction is being carried out in the reaction vessel.

At least one gas duct is preferably arranged in the reaction block, with which, in one position of the functional part, one or a plurality of reaction vessels are connected via the functional part so that they can be subjected to gas via the gas duct or a positive pressure or a depression can be generated in them via the gas duct. If only one gas duct is used, this has the advantage that only one gas supply system is required.

In an advantageous embodiment variant, the functional part can be adjusted into a position in which at least one reaction vessel is closed and at least one reaction vessel communicates with the gas duct. This permits, in particular, filtrations to be carried out, as is described in WO 98/57738.

At least two, preferably at least ten, reaction vessels are associated in parallel with a functional part. This permits the joint control of a plurality of parallel reactions.

In an advantageous embodiment variant, a plurality of functional parts are arranged in the reaction block, at least one reaction vessel being associated with each functional part and it being possible to actuate the functional parts individually, jointly or in groups. The use of a plurality of functional parts permits the individual control of the access to the individual reaction vessels or groups of reaction vessels. The reactions to be carried out can be further diversified by this means. It is particularly advantageous to design the actuation of the functional parts so that it is possible to switch between individual, joint or group actuation. It is then possible to realize an optimum control specific to the application. A joint or group actuation has the advantage that a plurality of functional parts can be operated by one drive motor.

The switch block according to the invention is described in more detail below with reference to the attached drawings using exemplary embodiments. In the drawings.

FIRST EXEMPLARY EMBODIMENT—FIGS. 1 TO 8

Figure 1:
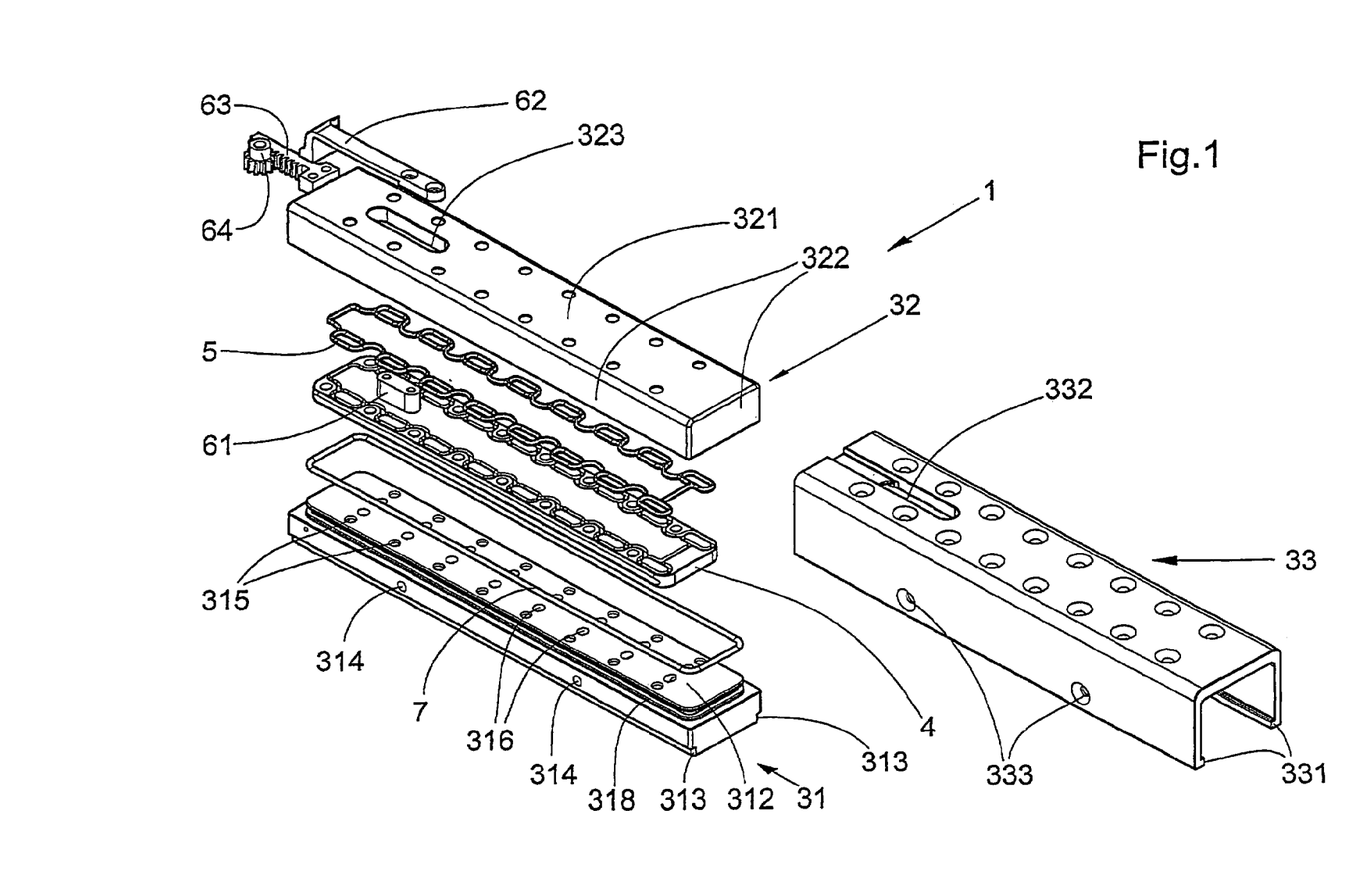
FIG. 1 shows, in an exploded view, a first exemplary embodiment of the switch block according to the invention with a slide plate as the functional part.
Figures 2, 3:
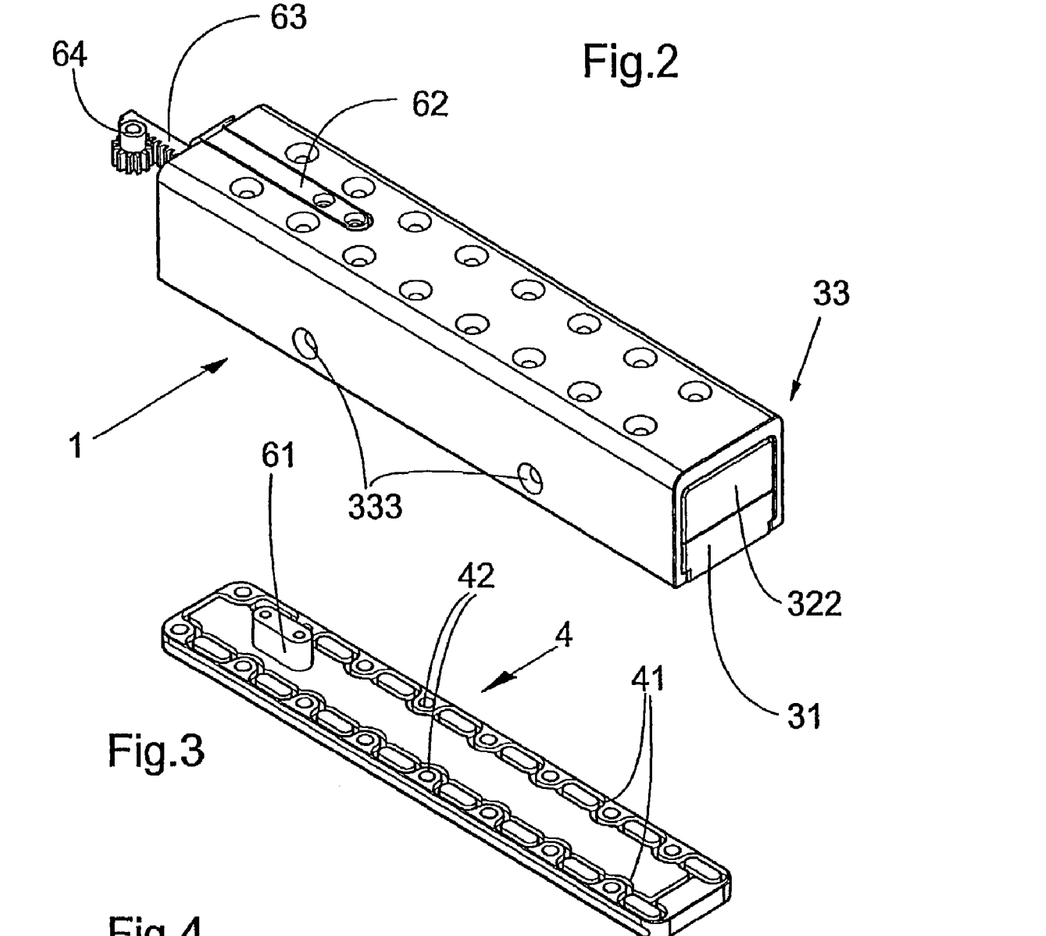
FIG. 2 shows the switch block of FIG. 1 in the assembled condition.
FIG. 3 shows the slide plate of the switch block of FIG. 1 from above in a perspective view.

In this first exemplary embodiment, a switch block 1 has a reaction plate 31 and a mating plate 32 with a slide plate 4 displaceably arranged between them. The mating plate 32 has a casing-type configuration with a cover plate 321 and four side walls 322 and, together with the reaction plate 31, encloses the slide plate 4, the side walls 322 being seated on the reaction plate 31, on the one hand, and being in contact, at the sides, with an upwardly protruding part 312 of the reaction plate 31, on the other. A sealing element 7, preferably made of plastic, rubber or a rubber-like material, is arranged, between the upwardly protruding part 312 and the side walls 322, in a groove 318 of the part 312. This sealing element 7 ensures that the mating plate 32 and the reaction plate 31 are in sealing contact with one another, particularly in the case of very high pressures of more than 250 bar. The mating plate 32 and the reaction plate 31 are held together by a retention profile section 33, which is pushed over the two plates, which are placed one above the other, two arms 331 of the retention profile section 33 engaging behind the reaction plate 31 and being in contact with shoulders 313 of the reaction plate 31. In addition, the retention profile section 33 is screwed onto the reaction plate 31 by means of screws (not shown) which are screwed into screw holes 333 in the retention profile section 33 and into screw holes 314 in the reaction plate 31.

The reaction plate 31, the mating plate 32 and the retention profile section 33 jointly form a reaction block, in which the slide plate 4 is displaceably secured. The adjustment of the slide plate 4 takes place by rotating a gearwheel 64, which engages in a toothed rack 63, to which an actuation rod 62 is screwed and which, at its other end, is screwed to an actuation spigot 61 screwed to the slide plate 4. The actuation spigot 61 protrudes through an elongated hole 323 in the cover plate 321 of the mating plate 32 and through an elongated hole 332 in the retention profile section 33, which elongated holes are respectively sufficiently long for the slide plate 4 to be displaced into all desired positions. The gearwheel 64 is, for example, driven by a stepper or linear motor (not shown).

Figure 7:
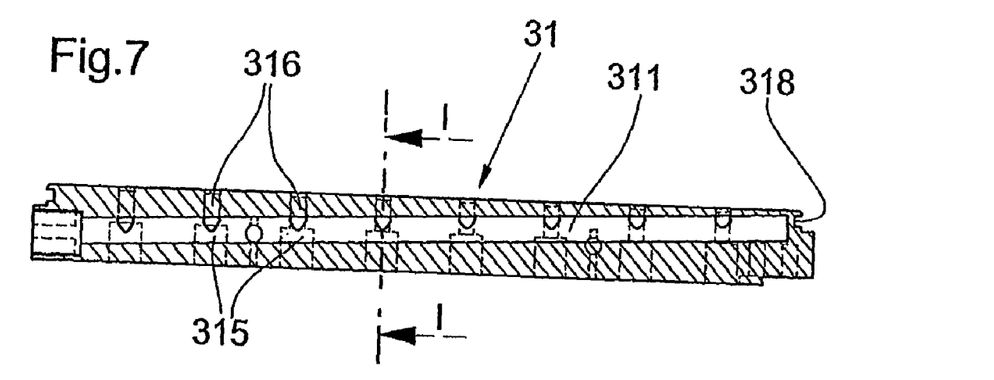
FIG. 7 shows a longitudinal section through a reaction plate of the switch block of FIG. 1.
Figure 8:
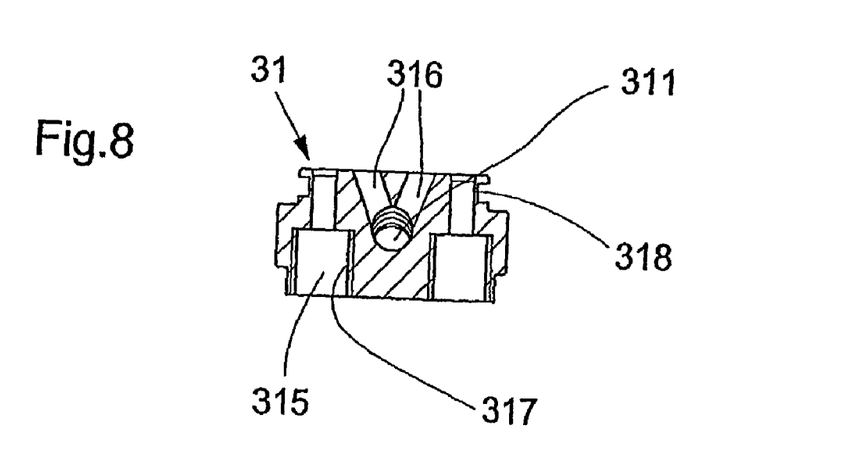
FIG. 8 shows the reaction plate of FIG. 7 in a sectional view along the line I-I in FIG. 7.

The reaction plate 31 is provided with through-holes 315, which are surrounded by threads 317 in their lower, wider part. Reaction vessels can be screwed to this lower part directly or by means of couplings. The reaction plate 31 has, furthermore, an advantageously obliquely extending gas duct 311 over almost its complete length, and also connection holes 316 which extend from the gas duct 311 to the upper side of the reaction plate 31. A corresponding number of vacuum pumps and gas supply devices can be connected to the open end of the gas duct 311 by means of a valve, preferably a multiple valve.

Figure 4:
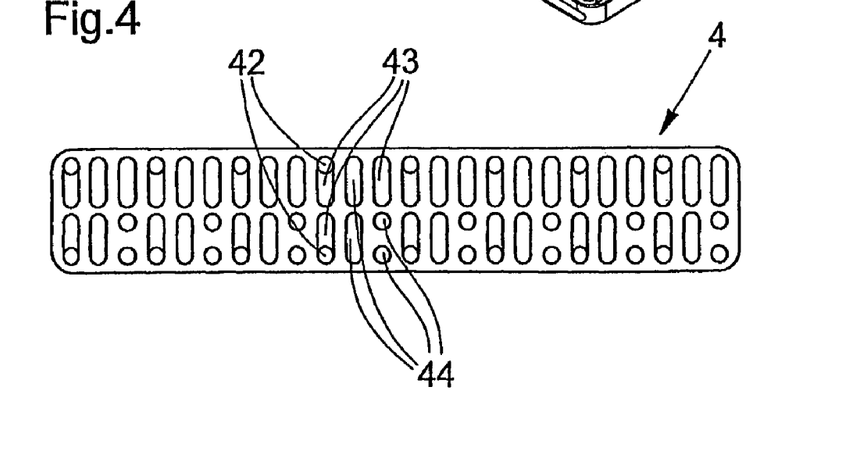
FIG. 4 shows the slide plate of FIG. 3 in a view from below.

The lower side of the slide plate 4, which is in contact with the reaction plate 31, has a pattern which is repeated eight times. A single pattern comprises three different arrangements of through-holes 42, depressions 43 and closing surfaces 44, which permit various functions in interaction with the reaction plate 31, such as, for example, the closing of one or a plurality of reaction vessels by means of the closing surfaces 44, leaving open one or a plurality of reaction vessels, so that a supply and/or removal tool, for example a needle, can be respectively introduced for the supply and/or removal of substances in these reaction vessels, and/or the connection of one or a plurality of reaction vessels to the gas duct 311 by means of depressions 43 and connection holes 316, in order to subject this reaction vessel or vessels to a gas or to expose it or them to positive pressure or depression.

The possible patterns for the slide plate 4, and therefore the possible functions in the various slide plate positions, are not explicitly described here because they do not represent the actual invention. Examples of switch blocks with suitable patterns are described in WO 98/57738 of the same applicant, this publication being therefore explicitly included in the present description.

Figures 5, 6:
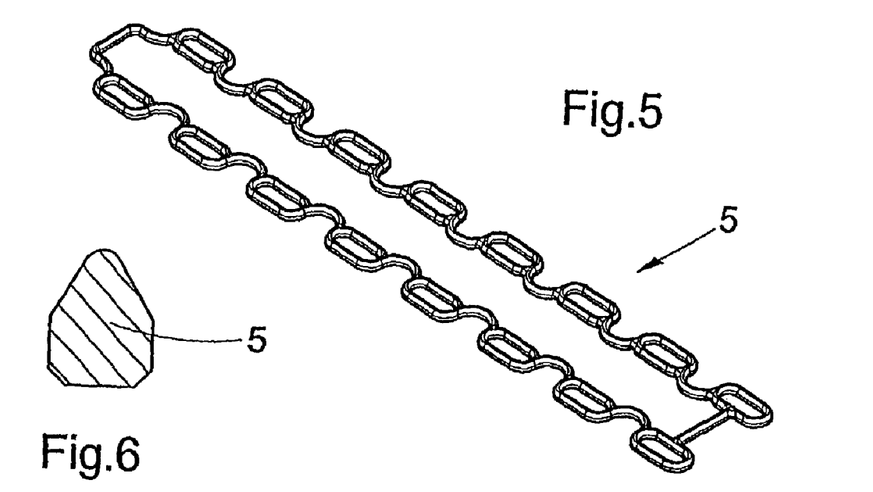
FIG. 5 shows a sealing element of the switch block of FIG. 1 in a perspective view.
FIG. 6 shows a cross section through the sealing element of FIG. 5.

So that the switch block 1 is sealed even in the case of high pressures extending to more than 250 bar, grooves 41, in which is arranged a sealing element 5, preferably made of plastic, rubber or a rubber-like material, are provided on the upper side of the slide plate 4. If a high positive pressure is generated in the reaction vessels, either directly or by means of the gas duct 311, the slide plate 4, together with the sealing element 5, is pressed upward against the cover plate 321 of the mating plate 32. The sealing element 5, which is then compressed in its height, ensures a seal, the decisive feature being that the sealing effect becomes greater as the pressure becomes higher because the sealing element 5 is more strongly compressed in its height in the case of higher pressure and, because of this, is in flatter contact and over a larger area with the cover plate 321. Although the tendency of a gas to penetrate between the sealing element 5 and the cover plate 321 and/or the slide plate 4 becomes greater at higher pressures, the slide plate 4 and/or the sealing element 5 are, simultaneously, also pressed more strongly from underneath onto the sealing element 5 and/or the cover plate 321 because of the higher pressure. The fact that the sealing effect becomes larger as the area subject to the pressure becomes larger then holds good. In order that a good sealing effect should be present even at small positive pressures, the sealing element preferably has a cross section which becomes narrower toward the top, as shown in FIG. 6.

In the case of a depression in the reaction vessels, the sealing of the switch block 1 is ensured by the mutually contacting surfaces of the slide plate 4 and the reaction plate 51 having a precise configuration, the surfaces being preferably treated with grease, oil or Teflon spray and being preferably as small as possible, as is described in WO 98/57738. The slide plate 4 is drawn onto the reaction plate 31 by the depression in the reaction vessels and, in fact, more strongly as the depression becomes deeper and the surface exposed to it becomes larger.

In principle, of course, it is also possible to provide a sealing element on the bottom side of the slide plate 4 and/or to configure the mutually contacting surfaces of the slide plate 4 and the cover plate 321 so precisely, to make them so small and, preferably, to treat them with grease, oil or Teflon spray such that they are in tight contact with one another even in the case of high pressure differences.

The sealing element 5 is configured and arranged in such a way that the through-holes 42 are located within the sealed region so that no gas can escape via them. It is of essential importance that the actuation spigot 61 should be fastened in a region of the slide plate 4 which is free of positive pressure and depression. This makes it possible to avoid having to employ additional sealing means for the actuation spigot 61 and/or the actuation rod 62 or having to integrate them in the actuation spigot 61 and/or the actuation rod 62, for example in the form of sealing lips. It is, on the other hand, quite possible to use a plurality of individual sealing elements instead of a single sealing element 5 between the slide plate 4 and the cover plate 321.

The following consideration applies to the whole of the further description. If, for the purpose of an unambiguous drawing arrangement, designations are contained in a figure but are not mentioned in the directly associated description text, reference should be made to their explanation in previous figure descriptions.

Figure 9A:
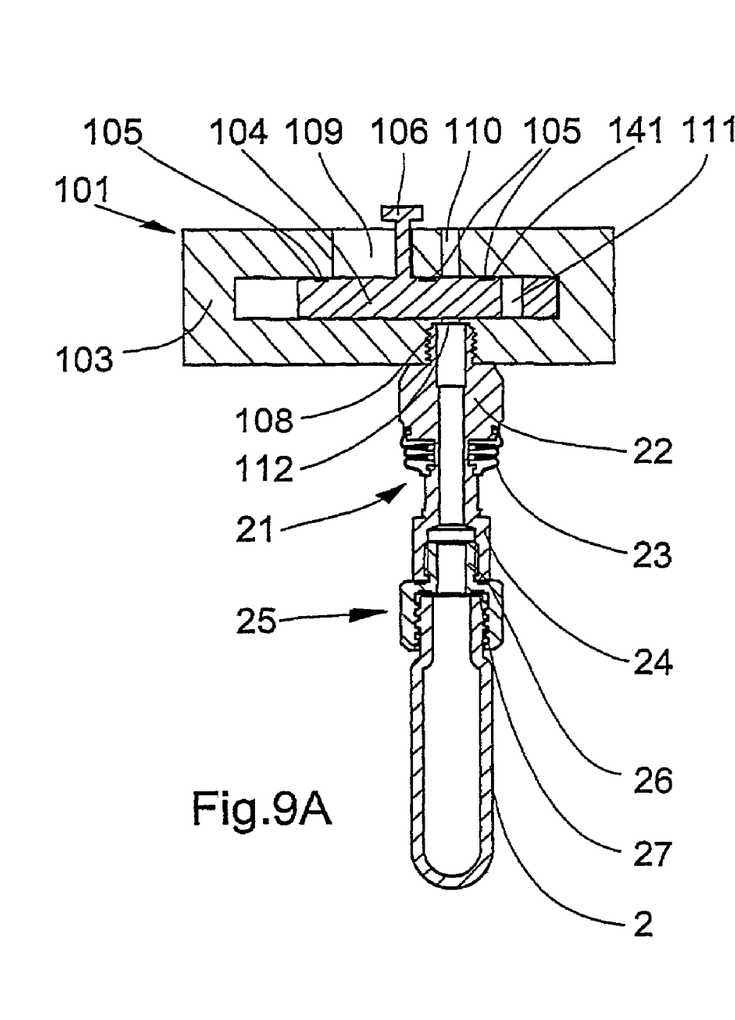
FIG. 9A shows a sectional view of a second exemplary embodiment of the switch block according to the invention with an attached reaction vessel, having a slide plate as the functional part and an actuation element which is applied to the functional part in a region free from positive pressure and depression, when the reaction vessel is closed.
Figure 9B:
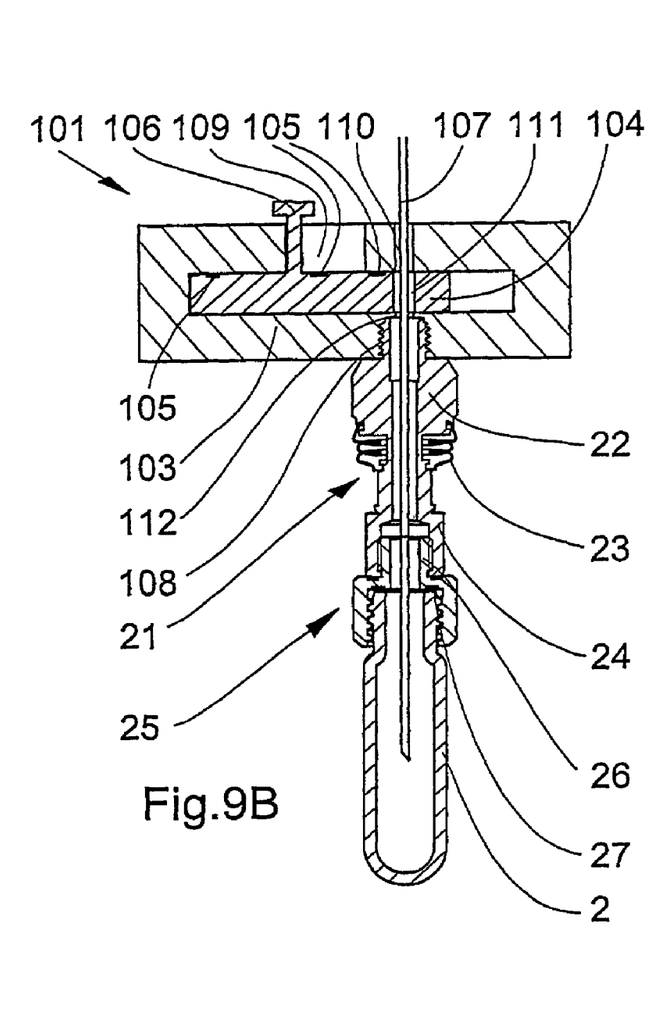
FIG. 9B shows a sectional view of the switch block with the reaction vessel of FIG. 9A when the reaction vessel is open, into which reaction vessel a supply and/or removal tool are introduced.

SECOND EXEMPLARY EMBODIMENT—FIGS. 9A AND 9B

In this second exemplary embodiment, a switch block 101 has a reaction block 103 in which a slide plate 104 is displaceably arranged. A flexible coupling 21, which comprises an upper part 22 and a lower part 24 which are movably connected together by means of a link 23, is screwed into a threaded hole 108 in the reaction block 103, which threaded hole 108 is abutted in the direction of the slide plate 104 by an unthreaded hole 112. The lower part 24 clamps around the head 26 of a connecting part 25, which has a threaded hole 27 into which a reaction vessel 2 is screwed. The reaction vessel 2 is preferably manufactured from metal, or glass in a metal casing, so that it can be subjected to high pressures.

The slide plate 104 can be adjusted by means of an actuation element 106 which, starting from the slide plate 104, extends to the outside through an elongated hole 109 in the reaction block 103. The actuation element 106 can, for example, be driven by means of a gearwheel and a toothed rack, as in the case of the first exemplary embodiment. In the case of the present exemplary embodiment, the actuation element 106 is again in contact with the slide plate 104 in a region which is pressure-free when the reaction vessel 2 is under positive pressure.

The slide plate 104 can take up two functional positions. In the first functional position, shown in FIG. 9A, the reaction vessel 2 is closed. Sealing elements 105, which are arranged in grooves 141 in the slide plate 104, seal the switch block 101 toward the outside and therefore ensure that no gas can pass from the reaction vessel 2 and/or the pressure-tight part of the switch block 101 to the elongated hole 109 and to a supply and/or removal hole 110 in the upper part of the reaction block 103.

In the second functional position shown in FIG. 9B, the reaction vessel 2 is open. A supply and/or removal tool 107, a needle in this case, is introduced into the reaction vessel 2 through the supply and/or removal hole 110, a through-hole 111 in the slide plate 104, the unthreaded hole 112, the threaded hole 108, the flexible coupling 21 and the connecting part 25.

Figure 10A:
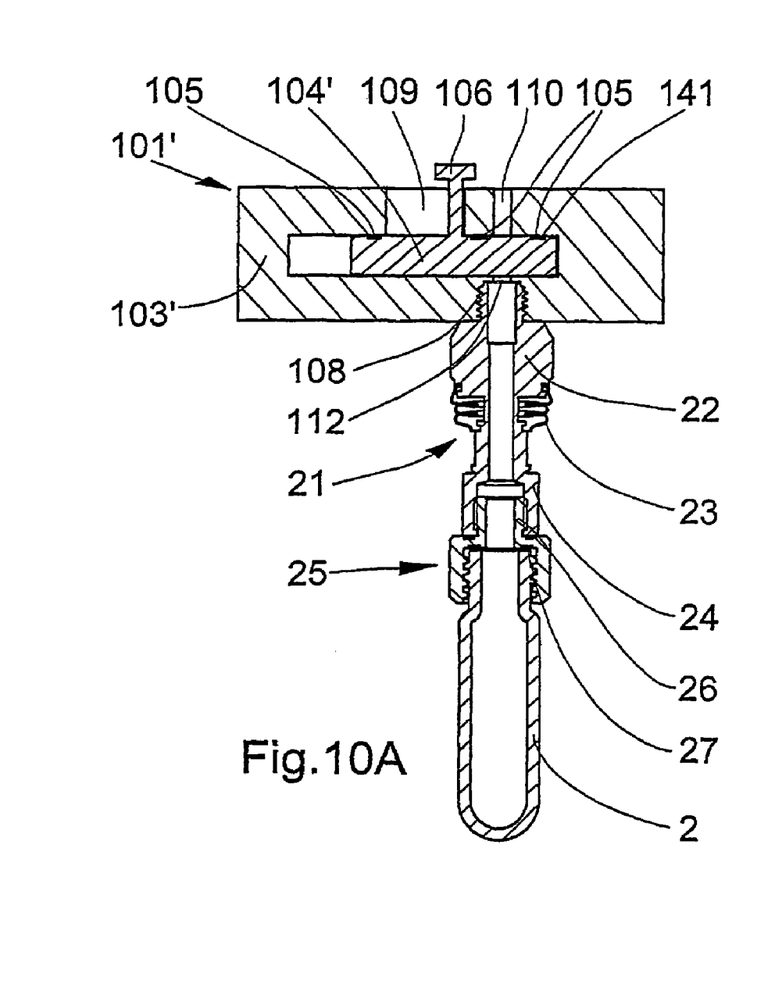
FIG. 10A shows a sectional view of a third exemplary embodiment of the switch block according to the invention with an attached reaction vessel, having a slide plate as the functional part and an actuation element which is applied to the functional part in a region free from positive pressure and depression, when the reaction vessel is closed.
Figure 10B:
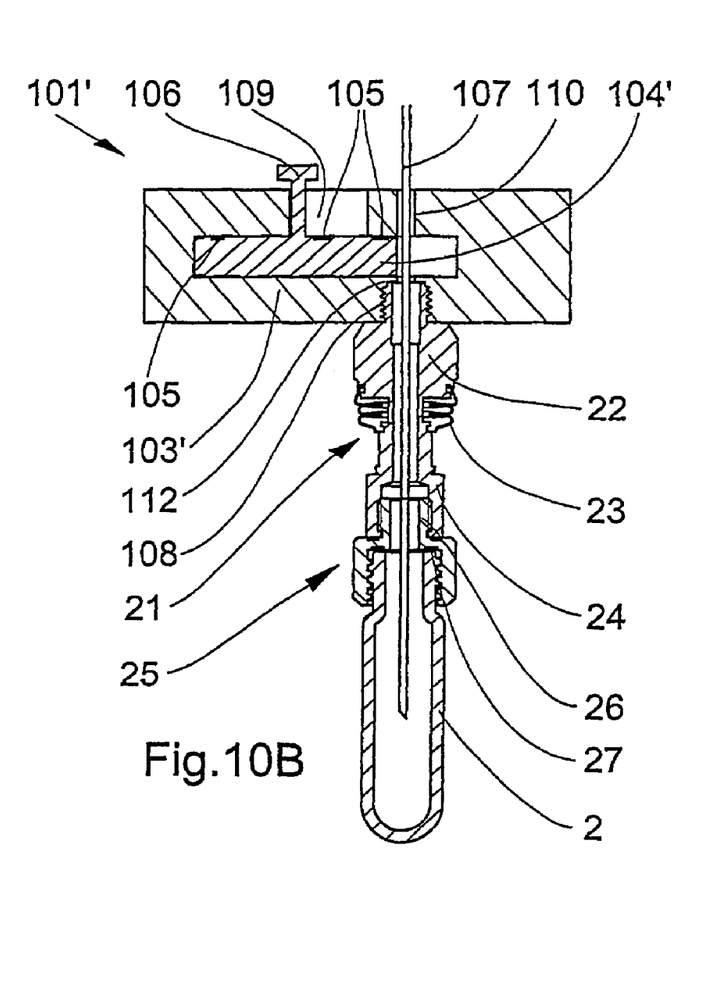
FIG. 10B shows a sectional view of the switch block with reaction vessel of FIG. 10A when the reaction vessel is open, into which reaction vessel a supply and/or removal tool are introduced.

THIRD EXEMPLARY EMBODIMENT—FIGS. 10A AND 10B

The switch block 101' of this third exemplary embodiment differs from the switch block 101 of the second exemplary embodiment only in the fact that the slide plate 104' does not have a through-hole 111 but is, instead, shorter. The supply and/or removal tool 107 is correspondingly introduced into the reaction vessel 2, as shown in FIG. 10B, through the supply and/or removal hole 110, adjacent to the slide plate 104' and through the unthreaded hole 112, the threaded hole 108, the flexible coupling 21 and the connecting part 25. Because of the shorter slide plate 104', the space accepting the slide plate 104' in the reaction block 103' is also shorter.

Figure 11:
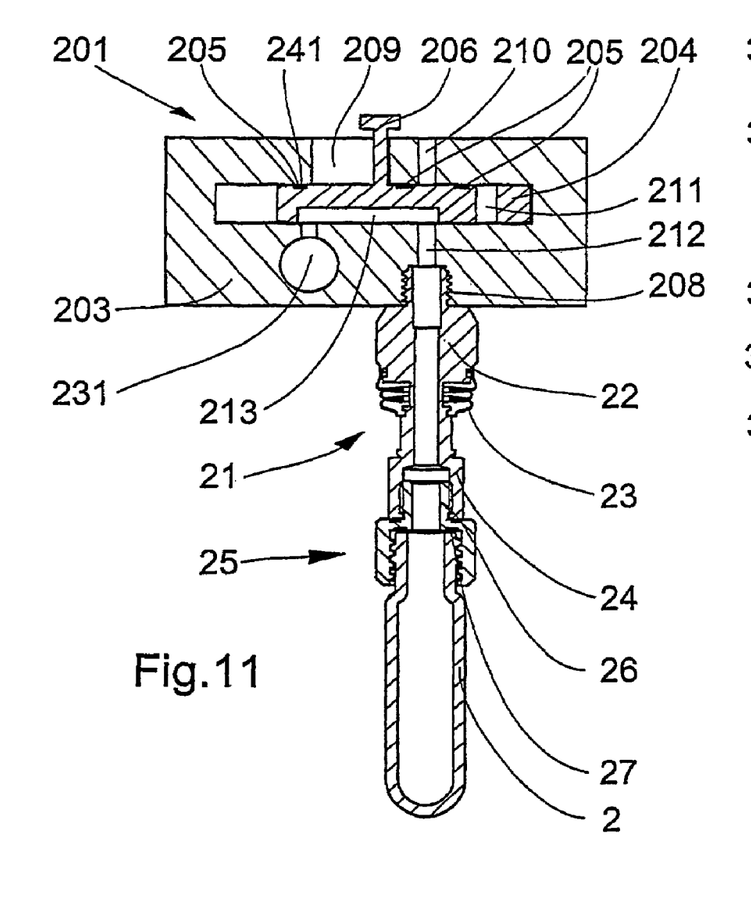
FIG. 11 shows a sectional view of a fourth exemplary embodiment of the switch block according to the invention with an attached reaction vessel, having a slide plate as the functional part and an actuation element which is applied to the functional part in a region free of positive pressure and depression, when the reaction vessel communicates with the gas duct.

FOURTH EXEMPLARY EMBODIMENT—FIG. 11

In this fourth exemplary embodiment, a switch block 201 has a reaction block 203 in which a slide plate 204 is displaceably arranged. A flexible coupling 21, which comprises an upper part 22 and a lower part 24 which are movably connected together by a link 23, is again screwed into a threaded hole 208 in the reaction block 203, which threaded hole 208 is abutted, in the direction toward the slide plate 204, by an unthreaded hole 212. The lower part 24 clamps around the head 26 of a connecting part 25, which has a threaded hole 27 into which a reaction vessel 2 is screwed. The reaction vessel 2 is preferably manufactured from metal, or glass in a metal casing, so that it can be subjected to high pressures. At pressures up to approximately 20 bar, in particular, it can also be manufactured from glass alone.

The slide plate 204 can, corresponding to the second exemplary embodiment, be adjusted by an actuation element 206 which, starting from the slide plate 204, extends to the outside through an elongated hole 209 in the reaction block 203. In the present exemplary embodiment, the actuation element 206 is again in contact with the slide plate 204 in a region which is pressure-free when the reaction vessel 2 is under positive pressure.

The slide plate 204 can take up two functional positions. In the first functional position shown, the reaction vessel 2 communicates, via a recess 213 in the slide plate 204, with a gas duct 231 in the reaction block 203. In this way, a gas can be supplied to or removed from the reaction vessel 2, and the reaction vessel 2 can, in particular, be subjected to a positive pressure or a depression can be generated in it. Sealing elements 205 arranged in grooves 241 in the slide plate 204 seal the switch block 201 toward the outside and therefore ensure that no gas from the reaction vessel 2 can pass to the elongated hole 209 and to a supply and/or removal hole 210 in the upper part of the reaction block 203.

In the second functional position (not shown), in which the slide plate 204 is pushed completely to the left, the reaction vessel 2 is open. A supply and/or removal tool can be introduced into the reaction vessel 2 through the supply and/or removal hole 210, a through-hole 211 in the slide plate 204, the unthreaded hole 212, the threaded hole 108, the flexible coupling 21 and the connecting part 25.

Figure 12:
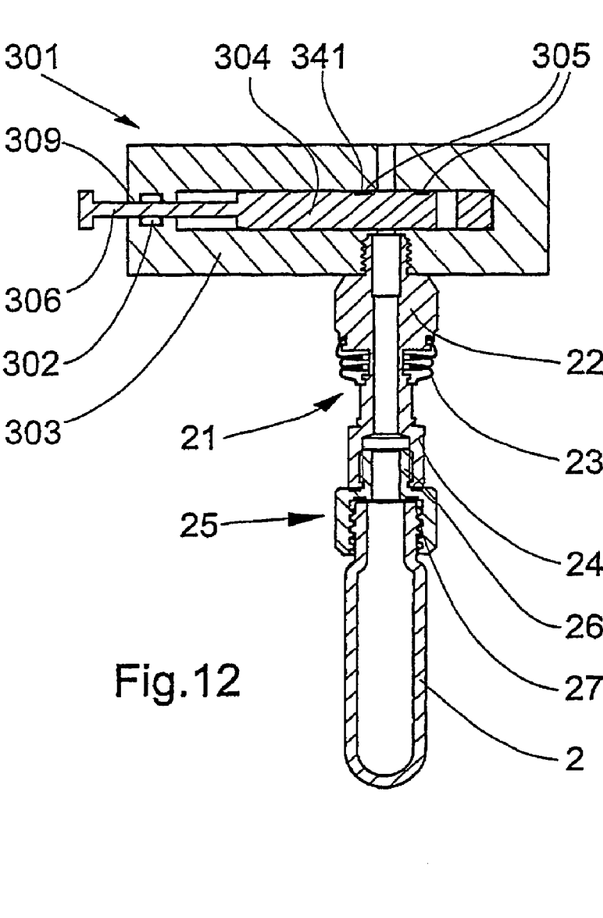
FIG. 12 shows a sectional view of a fifth exemplary embodiment of the switch block according to the invention with an attached reaction vessel, having a slide plate as the functional part and an actuation element which is applied to the functional part at the side.

FIFTH EXEMPLARY EMBODIMENT—FIG. 12

The switch block 301 of this fifth exemplary embodiment differs from the switch block 101 of the second exemplary embodiment only in the fact that the actuation element 306 is in contact at the side with the slide plate 304 and is led out of the reaction block 303 at the side through a hole 309. Although this dispenses with a sealing element 305, which is arranged in a groove 341, between the slide plate 304 and the reaction block 103, a separate and more complex radial sealing arrangement for leading the actuation element 306 through the reaction block 303 is necessary. In the present case, this takes place by means of a sealing element 302, preferably made of plastic, rubber or a rubber-like material. In contrast to the sealing element 305, the sealing element 302 is not compressed in the simple manner described above when there is a positive pressure in the reaction vessel 2; the sealing surface and the sealing force are not, therefore, increased.

Otherwise, what has been stated with respect to the second exemplary embodiment applies.

SIXTH EXEMPLARY EMBODIMENT—FIGS. 13 AND 15 TO 17

Figure 13:
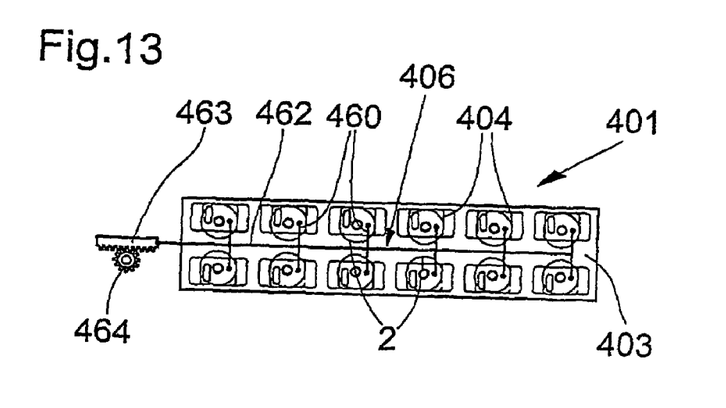
FIG. 13 shows a schematic view onto a sixth exemplary embodiment of the switch block according to the invention with attached reaction vessels, having a plurality of jointly actuated slide plates as functional parts.

In this case, a switch block 401 has a reaction block 403 in which twelve individual slide plates 404 are displaceably arranged. The adjustment of the slide plates 404 takes place jointly, in this exemplary embodiment, by means of an actuation element 406, which is actuated by a gearwheel 464 via a toothed rack 463. The gearwheel 464 is driven, for example, by a stepper or linear motor (not shown). The actuation element 406 comprises an actuation rod 462, which is connected to the toothed rack 463 and to which are fastened six transverse rods 460, which extend at right angles to the actuation rod 462. An actuation spigot 461, which is respectively connected to one of the slide plates 404, is respectively attached to each of the two ends of each of the transverse rods 460. In this way, all twelve slide plates 404 can be jointly activated.

Figure 15:
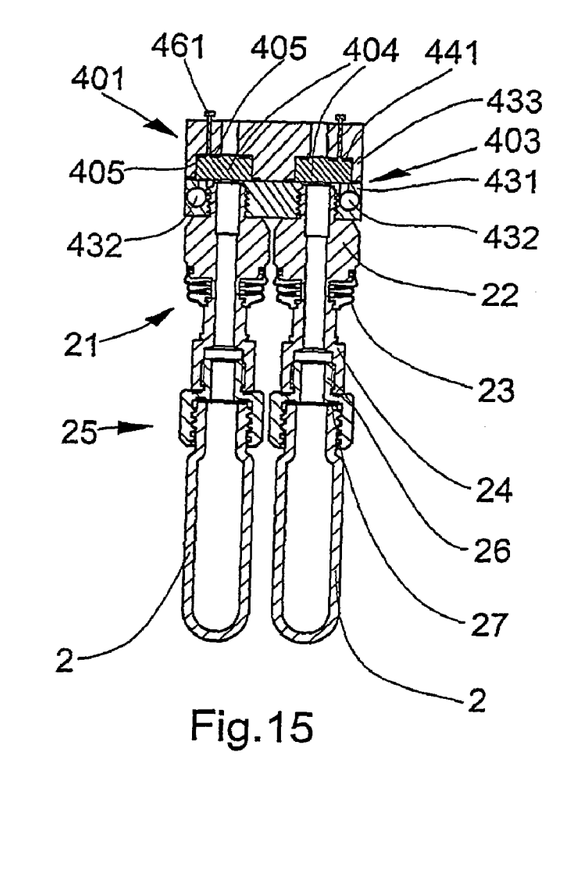
FIG. 15 shows a sectional view of the switch block with reaction vessels of FIG. 13 when the reaction vessels are closed.

The reaction block 403 is composed of two parts 431 and 433, which are welded together. A total of twelve reaction vessels 2 are screwed, in two parallel rows, into threaded holes 408 of the lower reaction block part 431 by means of connecting parts 25 and flexible couplings 21. Two gas ducts 432, by means of which gas can be supplied to or removed from the reaction vessels 2 and by means of which, in particular, a depression or positive pressure can be generated, are also arranged in the lower reaction block part 431.

The individual slide plates 404 can take up three different functional positions. In the first functional position shown in FIG. 15, the reaction vessels 2 are closed. Sealing elements 405 arranged in grooves 441 in the slide plates 404 seal the switch block 401 toward the outside and therefore ensure that no gas from the reaction vessels 2 escapes from the switch block 401.

Figures 16, 17:
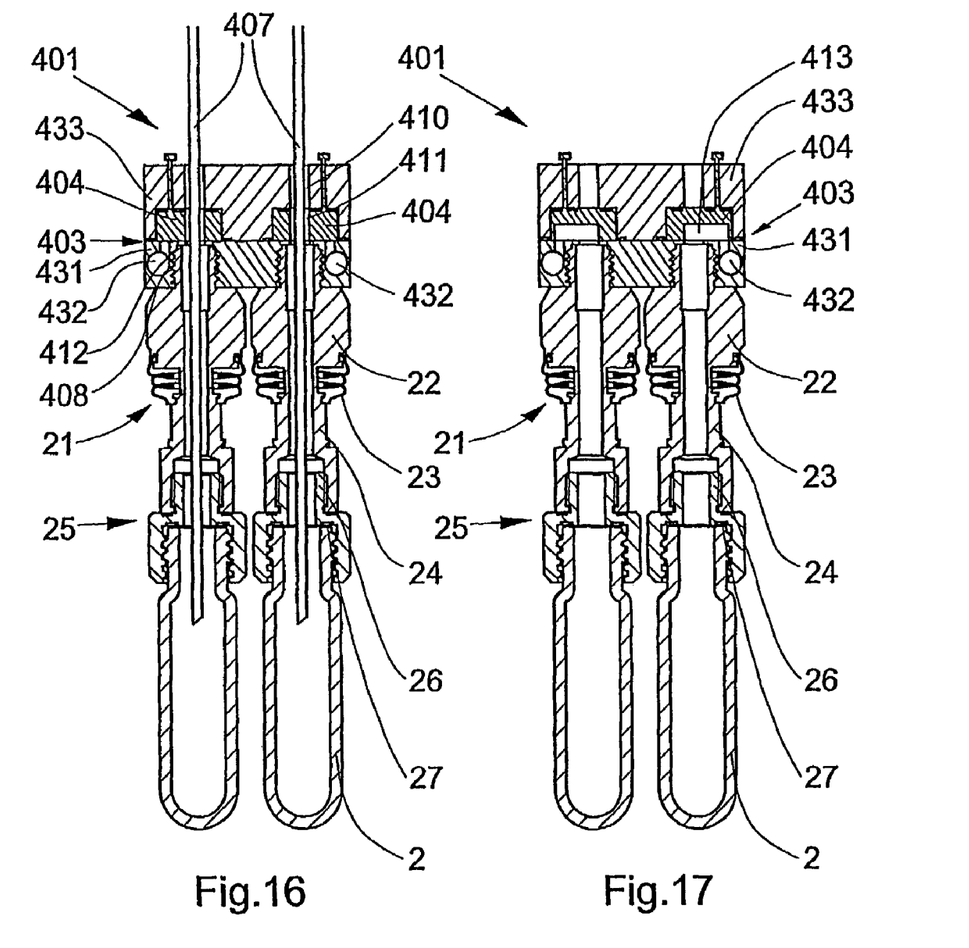
FIG. 16 shows a sectional view of the switch block with reaction vessels of FIG. 13 when the reaction vessels are open, into which reaction vessels supply and/or removal tools are introduced.
FIG. 17 shows a sectional view of the switch block with reaction vessels of FIG. 13 when the reaction vessels communicate with gas ducts.

In the second functional position shown in FIG. 16, the reaction vessels 2 are open. A supply and/or removal tool 107, a needle in this case, is introduced in each case into the reaction vessels 2 through a supply and/or removal hole 410 in the upper reaction block part 433 and through a through-hole 411 in the slide plate 404, an unthreaded hole 412, the threaded hole 408, the flexible coupling 21 and the connecting part 25.

In the third functional position, which is shown in FIG. 17, the reaction vessels 2 respectively communicate with one of the gas ducts 432 via a recess 413 in the slide plates 404. In this way, a gas can be supplied to or removed from the reaction vessels 2 and, in particular, they can be subjected to a positive pressure or a depression can be generated in them.

Figure 14:
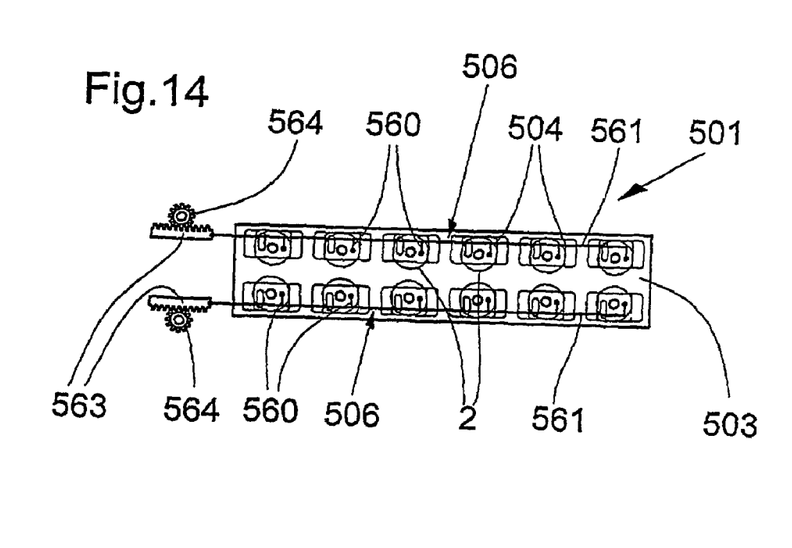
FIG. 14 shows a schematic view onto a seventh exemplary embodiment of the switch block according to the invention with attached reaction vessels, having two groups of jointly actuated slide plates as functional parts.

SEVENTH EXEMPLARY EMBODIMENT—FIG. 14

In the case of this switch block 501, and as a difference relative to the sixth exemplary embodiment, the twelve slide plates 504 arranged in the reaction block 503 are not all jointly actuated but, rather, actuation is provided in two groups. The adjustment of one group of the slide plates 504 takes place by means of a respective actuation element 506, which is actuated by a gearwheel 564 via a toothed rack 563. The gearwheel 564 is driven, for example, by a stepper or linear motor (not shown). The actuation element 506 comprises an actuation rod 561, which is connected to the toothed rack 563 and to which are fastened six transverse rods 560 extending at right angles to the actuation rod 561. An actuation spigot, which is respectively connected to one of the slide plates 504, is attached to the respective end of each transverse rod 560 which is not attached to the actuation rod 561.

In this way, six slide plates 504 can be jointly adjusted in each case.

Figure 18:
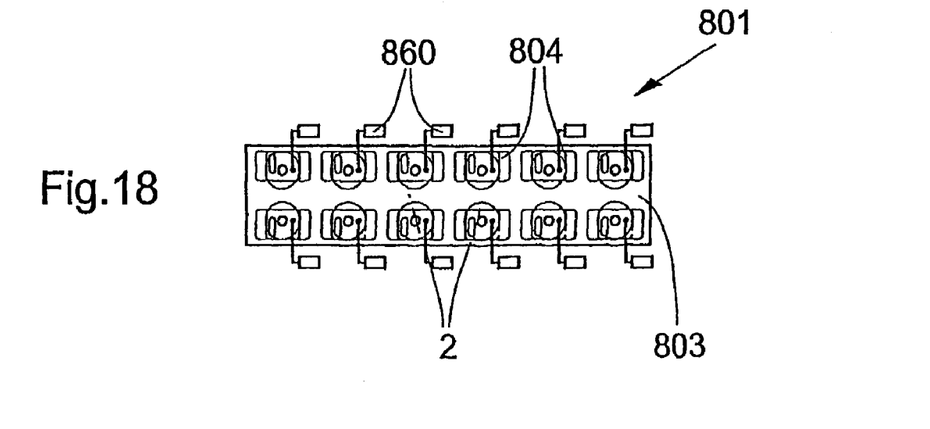
FIG. 18 shows a schematic view onto an eighth exemplary embodiment of the switch block according to the invention with attached reaction vessels, having individually actuated slide plates as functional parts.
Figures 19, 20:
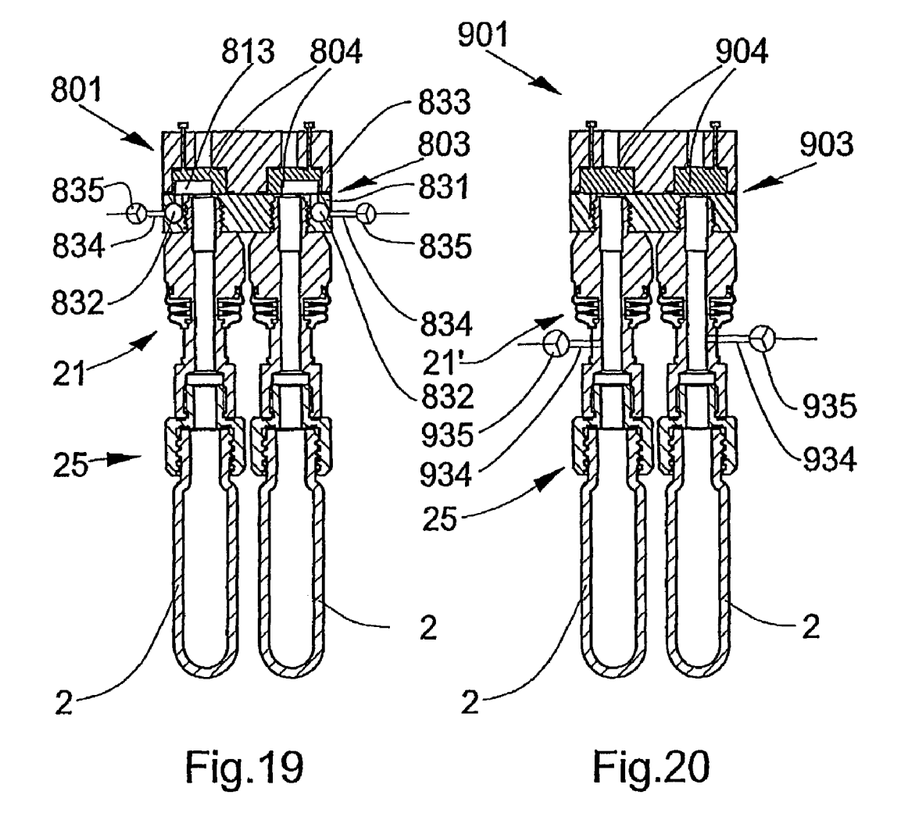
FIG. 19 shows a sectional view of the switch block with reaction vessels of FIG. 18 when the reaction vessels communicate with gas ducts.
FIG. 20 shows a sectional view of a ninth exemplary embodiment of a switch block with reaction vessels when the reaction vessels are closed.

EIGHTH EXEMPLARY EMBODIMENT—FIGS. 18 AND 19

In the case of this switch block 801, and as a difference relative to the sixth exemplary embodiment, the twelve slide plates 804 arranged in the reaction block 803 are not all jointly actuated but, rather, each slide plate 804 is adjusted by its own motor 860. The reaction block 803 is composed of two parts 831 and 833 which are welded together. A total of twelve reaction vessels 2 are screwed in two parallel rows, by means of connecting parts 25 and flexible couplings 21, into threaded holes in the lower reaction block part 831. Twelve gas ducts 832, one for each reaction vessel 2, are arranged in the lower reaction block part 831. Each gas duct 832 is connected, via a gas line 834, to a multipath valve 835, by means of which the supply or removal of gas and, in particular, the generation of a depression or positive pressure in the reaction vessel 2 can be individually controlled.

As in the case of the sixth exemplary embodiment, the individual slide plates 804 can take up three different functional positions. In the third functional position shown in FIG. 19, the reaction vessels 2 respectively communicate, via a recess 813 in the slide plates 804, with one of the gas ducts 832. A gas can be supplied to or removed from the reaction vessels 2 in this way and, in particular, they can be subjected to a positive pressure or a depression can be generated in them.

Otherwise, what has been stated with respect to the sixth exemplary embodiment applies.

NINTH EXEMPLARY EMBODIMENT—FIG. 20

As in the case of the eight exemplary embodiment, the twelve slide plates 904 arranged in the reaction block 903 are respectively adjusted by their own motors in this switch block 901. In this case, however, the reaction block 903 does not have any gas ducts and the slide plates 904 do not have any recesses. This embodiment dispenses with the third functional position. Each reaction vessel 2 is, instead, connected via the flexible coupling 21' and a gas line 934 opening into the latter, to a multipath valve 935, by means of which the supply or removal of gas and, in particular, the generation of a depression or positive pressure in the reaction vessel 2 can be individually controlled.

The individual slide plates 904 take up either the open functional position shown or a closed functional position, both of which are described in association with the sixth exemplary embodiment.

Figure 21:
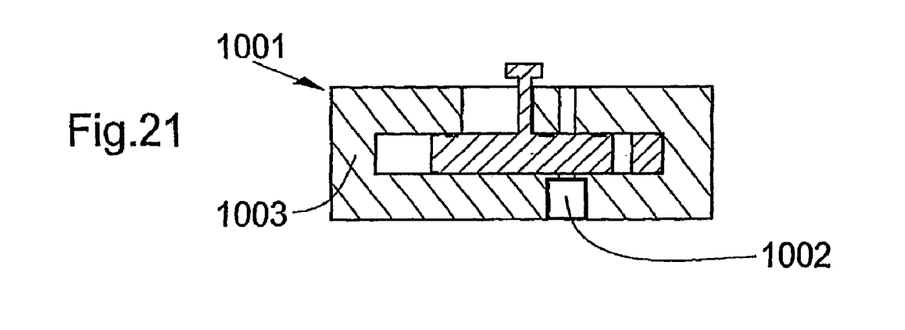
FIG. 21 shows a sectional view of a tenth exemplary embodiment of the switch block according to the invention with an integrated reaction vessel.

TENTH EXEMPLARY EMBODIMENT—FIG. 21

As a difference relative to the second exemplary embodiment, a reaction vessel 1002 is integrated directly into the reaction block 1003 of the switch block 1001 in this case. Otherwise, what has been stated with respect to the second exemplary embodiment applies.

Such integrated reaction vessels can also be provided instead of the reaction vessels 2 in the case of the other exemplary embodiments.

ELEVENTH EXEMPLARY EMBODIMENT—FIGS. 22 TO 25

In this eleventh exemplary embodiment, a functional part in the form of a ball 604 is rotatably arranged in a reaction block 603. A reaction vessel 2 (not shown) is screwed to the reaction block 603 by means of a connecting part and a flexible coupling with an upper part 22, as in the previous exemplary embodiments. The ball 604 can be adjusted by means of a rotary pin 606, which is provided with a positioning pin 602 and protrudes to the outside through the reaction block 603. It can take up two functional positions.

Figures 22, 23:
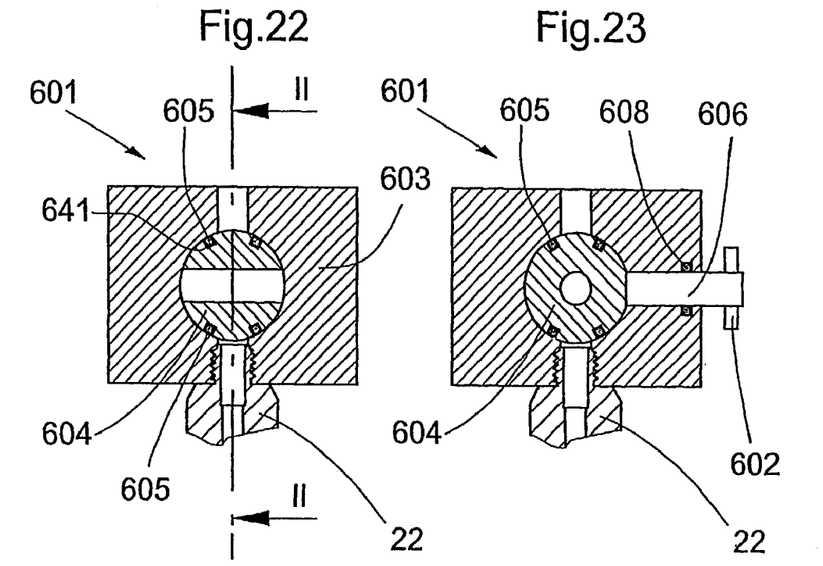
FIG. 22 shows a sectional view of an eleventh exemplary embodiment of the switch block according to the invention with an attached reaction vessel (only partially represented), with a rotatable ball as functional part, when the reaction vessel is closed.
FIG. 23 shows a sectional view, along the line II-II in FIG. 22, of the switch block with reaction vessels of FIG. 22.

In the first functional position shown in FIGS. 22 and 23, the reaction vessel 2 is closed. Sealing elements 605, which are arranged in grooves 641 in the ball 604, and a further sealing element 608, which is arranged around the rotary pin 606 in an annular groove in the reaction block 603, seal the switch block 601 toward the outside and therefore ensure that no gas from the reaction vessel 2 escapes from the switch block 601, should the pressure in the reaction vessel 2 be larger than the pressure outside the switch block 601.

Figures 24, 25:
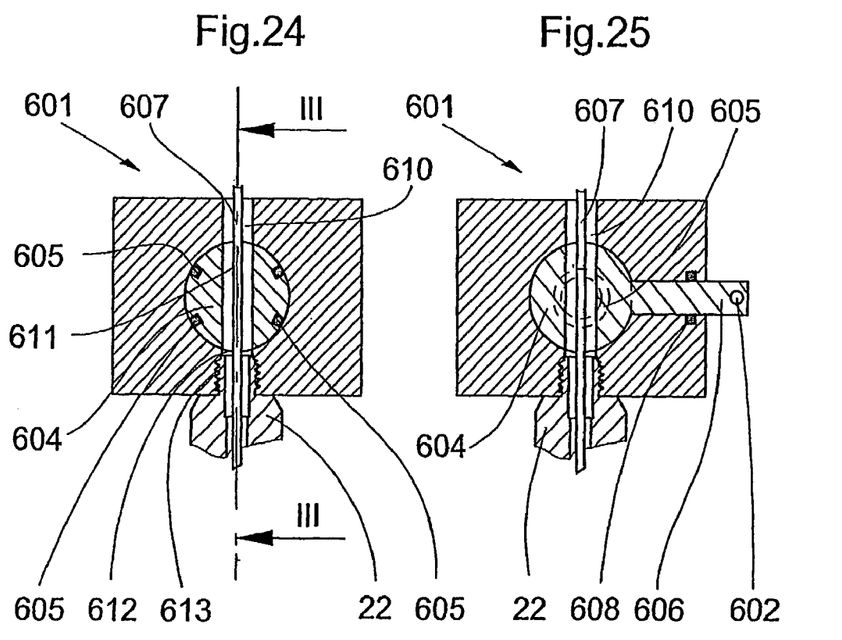
FIG. 24 shows a sectional view of the switch block with reaction vessel of FIG. 22 with an open reaction vessel, into which a supply and/or removal tool is introduced.
FIG. 25 shows a sectional view, along the line III-III in FIG. 24, of the switch block with reaction vessel of FIG. 24.

In the second functional position shown in FIGS. 24 and 25, the reaction vessel 2 is open. A supply and/or removal tool 607, a needle in this case, is introduced into the reaction vessel 2 through a supply and/or removal hole 610 in the reaction block 603, a through-hole 611 in the ball 604, an unthreaded hole 612, a threaded hole 613, the flexible coupling 21 (only partially visible) and the connecting part 25 (not shown).

Figure 26:
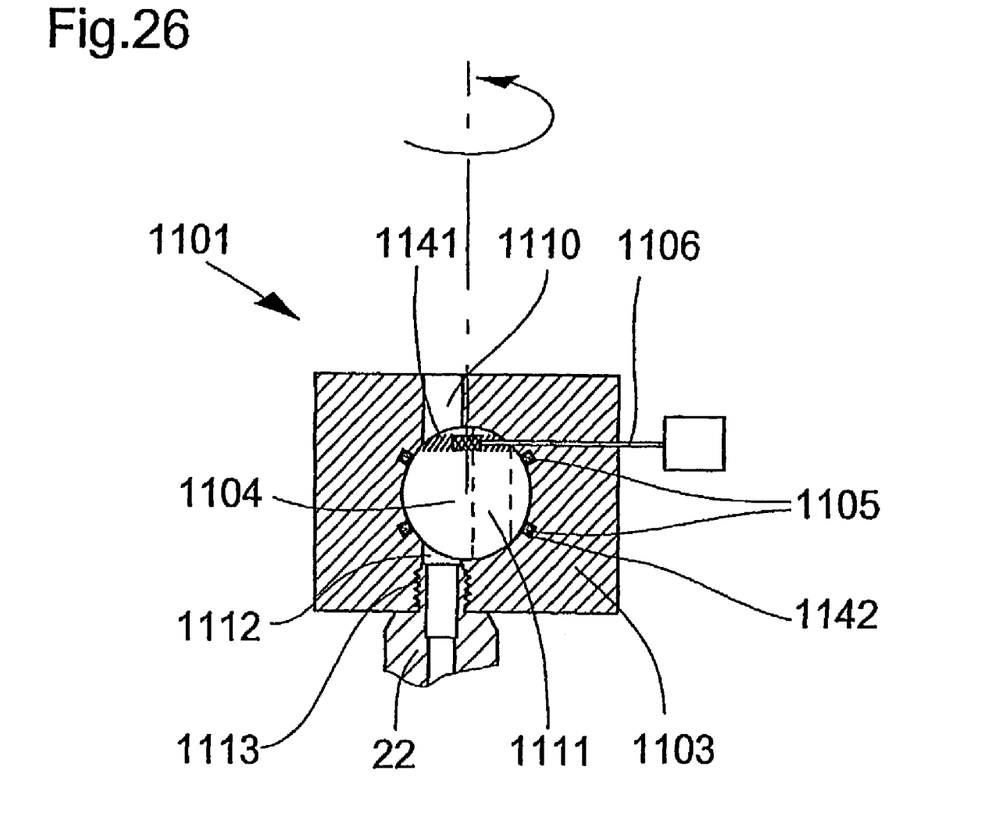
FIG. 26 shows a sectional view of a twelfth exemplary embodiment of the switch block according to the invention with an integrated reaction vessel.

TWELFTH EXEMPLARY EMBODIMENT—FIG. 26

In the case of this twelfth exemplary embodiment, a functional part in the form of a ball 1104 is rotatably arranged in a reaction block 1103. As in the previous exemplary embodiments, a reaction vessel 2 (not shown) is screwed with an upper part 22 to the reaction block 1103 by means of a connecting part and a flexible coupling. The ball 1104 is provided with a toothed ring 1141 and can be adjusted with this by means of an adjustment spindle 1106, which protrudes to the outside through the reaction block 1103. It is guided in the axis of rotation which has been included in the drawing, for example by means of a mandrel at the bottom and the top.

The ball 1104 can take up two functional positions. In the first functional position shown, the reaction vessel is closed. Sealing elements 1105 arranged in grooves 1142 in the ball 1104 seal the switch block 1101 toward the outside and, therefore, ensure that no gas from the reaction vessel 2 escapes from the switch block 1101. Because of the arrangement of the toothed ring 1141 above the two sealing elements 1105, the adjustment spindle 1106 is in contact with the ball 1104 in a region which is free from positive pressure and depression and its passage through the ball 1104 does not, therefore, need to be additionally sealed.

After rotation of the ball 1104 by 180°, a decentrally arranged through-hole 1111 in the ball 1104 connects a supply and/or removal hole 1110 in the reaction block 1103 to an unthreaded hole 1112 and a threaded hole 1113 in the reaction block 1103, so that a supply and/or removal tool (not shown) can be introduced into the reaction vessel.

THIRTEENTH EXEMPLARY EMBODIMENT—FIGS. 27 TO 30

In this thirteenth exemplary embodiment, a functional part in the form of a cylinder 704 is rotatably arranged in a reaction block 703. As in the preceding exemplary embodiments, a reaction vessel 2 (not shown) is screwed with an upper part 22 to the reaction block 703 by means of a connecting part and a flexible coupling. The cylinder 704, which protrudes to the outside through the reaction block 703, can be adjusted by means of a contact stud 702. It can take up two functional positions.

Figures 27, 28:
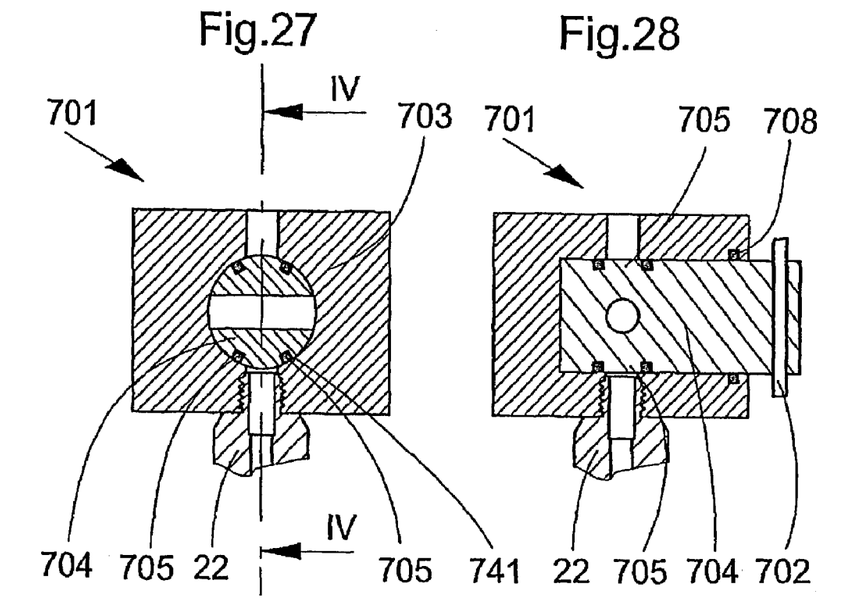
FIG. 27 shows a sectional view of a thirteenth exemplary embodiment of the switch block according to the invention with an attached reaction vessel (only partially represented), having a rotatable cylinder as functional part, when the reaction vessel is closed.
FIG. 28 shows a sectional view, along the line IV-IV in FIG. 27, of the switch block with reaction vessel of FIG. 27.

In the first functional position shown in FIGS. 27 and 28, the reaction vessel 2 is closed. Sealing elements 705, which are arranged in grooves 741 in the cylinder 704, and a further sealing element 708, which is arranged around the cylinder 704 in an annular groove in the reaction block 703, seal the switch block 701 toward the outside and, therefore, ensure that no gas from the reaction vessel 2 escapes from the switch block 701.

Figure 29:
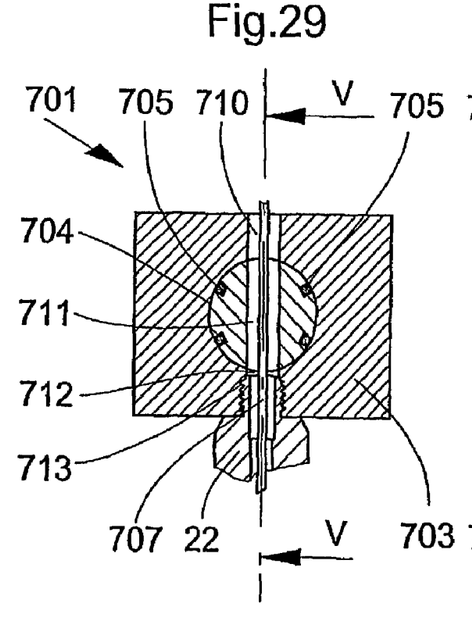
FIG. 29 shows a sectional view of the switch block with reaction vessel of FIG. 27 when the reaction vessel is open, into which reaction vessel a supply and/or removal tool is introduced.
Figure 30:
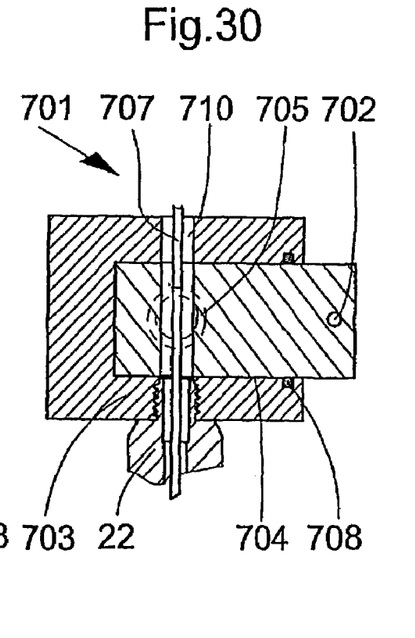
FIG. 30 shows a sectional view, along the line V-V in FIG. 29, of the switch block with reaction vessel of FIG. 29.

In the second functional position shown in FIGS. 29 and 30, the reaction vessel 2 is open. A supply and/or removal tool 707, a needle in this case, is introduced into the reaction vessel 2 through a supply and/or removal hole 710 in the reaction block 703, a through-hole 711 in the ball 704, an unthreaded hole 712, a threaded hole 713, the flexible coupling 21 (only partially visible) and the connecting part 25 (not shown).

Further design variants can be realized on the previously described switch blocks with reaction vessels according to the invention. In this connection, the following should still be expressly mentioned:

The slide plates 4; 104; 204; 304; 404; 504; 804; 904, the rotatable balls 604; 1104 or the rotatable cylinder 704 could be made of an elastic or soft material, for example rubber, or of graphite, so that additional sealing elements become superfluous.

With respect to functionality pattern, the individual slide plates 404, 504 and/or 804 of the switch blocks 401, 501 and/or 801 do not necessarily need to have the same configuration and can exhibit different functional positions.

The invention claimed is:

1. A switch block having at least two attached or integrated reaction vessels, the switch block comprising:
 a stationary part;
 wherein the stationary part is capable of having at least two attached or integral reaction vessels;
 a movable member mounted within the stationary part, the movable member being capable of being disposed in an open position so that, when a reaction vessel is attached or integral with the stationary part, the interior of the reaction vessel can be accessed in a straight line;
 a resilient element that is arranged between the stationary part and the moveable member, at least a portion of the resilient element being in contact with a mounting surface that is defined in either the movable member or the stationary part;

the movable member also being capable of being disposed in a closed position so that, when a reaction vessel is attached or integral with the stationary part, the interior of the reaction vessel cannot be accessed and a seal is created between the movable member, the resilient element, and the stationary part, the seal isolating the interior of the reaction vessel from outside of the switch block; and wherein the stationary part, the resilient element, and the movable member are arranged with respect to each other so that, when the movable member is disposed in the closed position, and when at least one reaction vessel is attached or integral with the stationary part, (i) the stationary part limits the movement of the movable member in a direction along the straight line to seal the movable member with respect to the stationary part in a pressure-tight manner thereby preventing an increase or decrease in pressure inside of the reaction vessel from breaking the pressure-tight seal which isolates the interior of the reaction vessel from outside of the switch block, and (ii) an increase in pressure inside the reaction vessel causes the movable member to move in a direction along the straight line to compress the resilient element between the stationary part and the moveable member to thereby increase the strength of the pressure-tight seal.

2. The switch block of claim 1, wherein the movable member is a slide plate that is displaceable relative to the stationary part along a minor axis of the switch block between an open position and a closed position.

3. The switch block of claim 1, wherein the moveable member is a slide plate that is displaceable along a major axis of the switch block between an open position and a closed position.

4. The switch block of claim 1, wherein the moveable member is rotatable between an open position and a closed position.

5. The switch block of claim 1, wherein a plurality of movable members are arranged in a reaction block, at least one reaction vessel being associated with each movable member, said movable members configured to be actuated individually, jointly or in groups.

6. The switch block of claim 1, wherein the stationary part is made up of two or more parts, which can be disassembled and between which the moveable member is arranged.

7. The switch block of claim 1, wherein, when the movable member is in the open position, a supply and/or removal tool and/or a probe can be introduced through the switch block into the at least one reaction vessel.

8. The switch block of claim 1, wherein mutually contacting surfaces of the moveable member and the stationary part are configured to sealingly contact each other on at least one side, the surfaces being treated with grease, oil or lubricating spray, the mutually contacting surfaces being smaller than the complete sides facing each other.

9. The switch block of claim 1, wherein an actuation element engages the moveable member, the actuation element extending through the stationary part and further extending beyond the stationary part, the actuation element being disposed in a region that is not subject to positive or negative pressures.

10. The switch block of claim 1, wherein the stationary part contains at least one gas duct operatively connected to one or more reaction vessels via the movable member, to subject the one or more reaction vessels to a gas via the gas duct, or to a positive or negative pressure via the gas duct.

11. The switch block of claim 10, wherein the movable member seals off at least one reaction vessel and at the same time operatively connects at least one reaction vessel to the gas duct.

12. The switch block of claim 1, wherein between two and ten reaction vessels are associated in parallel with the movable member.

13. The switch block of claim 1, wherein the stationary part is configured in one piece.

14. The switch block of claim 1, wherein the movable member is oriented within the stationary part such that a positive pressure in a reaction vessel will force the movable member away from the reaction vessel and toward the stationary part, thus increasing the strength of the pressure-tight seal.

15. The switch block of claim 1, wherein the movable member is oriented within the stationary part such that a negative pressure in a reaction vessel will suck the movable member toward the stationary part, thus increasing the strength of the pressure-tight seal.

16. The switch block of claim 1, wherein, when the movable member is disposed in the open position, and when a reaction vessel is attached or integral with the stationary part, a straight path is defined through the switch block to the interior of the reaction vessel.

17. The switch block of claim 1, wherein the movable member is arranged with clearance in the stationary part such that the movable member is not in gas-tight contact with the stationary part on at least one side at normal pressure.

18. The switch block of claim 1, wherein the stationary part comprises a reaction block.

19. The switch block of claim 1, wherein the movable member comprises a functional part.

20. The switch block of claim 1, wherein the mounting surface defined in either the moveable member or in the stationary part is defined by grooves that are formed in the moveable member or in the stationary part.

* * * * *